United States Patent [19]

Schneider et al.

[11] Patent Number: 5,686,388

[45] Date of Patent: Nov. 11, 1997

[54] CONCENTRATED STABLE SUSPENSION OF HERBICIDALLY ACTIVE 1,3,5-TRIAZINES AND PYRIDATE

[76] Inventors: Rudolf Schneider, Riesenederfeld 17, A-4040 Linz; Harald Leitner, Kirchstetten 19, A-4064 Oftering; Hermann Tramberger, Voralpensiedlung 16, A-3350 Haag; Michael Sturm, Welser Strasse 42; Engelbert Auer, Haltestellenweg 19a, both of A-4060 Leonding, all of Austria

[21] Appl. No.: 505,720

[22] Filed: Jul. 21, 1995

[30] Foreign Application Priority Data

Jul. 25, 1994 [AT] Austria ............................ 1466/94

[51] Int. Cl.⁶ .......................... A01N 43/66; A01N 43/58
[52] U.S. Cl. ............................................... 504/134
[58] Field of Search .................................... 504/134

[56] References Cited

U.S. PATENT DOCUMENTS

| | | | |
|---|---|---|---|
| 4,931,085 | 6/1990 | Wilson | 71/92 |
| 5,238,604 | 8/1993 | Hazen et al. | 252/356 |
| 5,446,013 | 8/1995 | Zurmühlen et al. | 504/242 |

FOREIGN PATENT DOCUMENTS

| | | |
|---|---|---|
| 009616 | 8/1979 | European Pat. Off. . |
| 165393 | 4/1985 | European Pat. Off. . |
| 554015 | 1/1993 | European Pat. Off. . |
| 394847 | 11/1993 | European Pat. Off. . |
| 9206596 | 4/1992 | WIPO . |

OTHER PUBLICATIONS

*The Agrochemicals Handbook.* "Pyridate." 1987.
Z. Pfl. Krakh. Pfl. Schutz, SonderH. XII, 1990, 509–514.
Research Disclosure 299, No. 031, p. 174 Mar. 1989.
Derwent Abstracts AN 82–12589E (JP-A-47 002 202) (1982).
CA101(23):205965u, 1983.
CA120(13):156580w, 1993.
CA101(21):180021q, 1984.
CA104(25):220695m, 1986.

*Primary Examiner*—S. Mark Clardy
*Attorney, Agent, or Firm*—Lynn Marcus-Wyner

[57] ABSTRACT

Concentrated, stable suspension of herbicidally active 1,3,5-triazines in a solution of pyridate in organic solvents or mixtures thereof, in which at 0° C. pyridate is at least 10% by weight soluble and the 1,3,5-triazines are at most 1% by weight soluble, together with emulsifiers, as well as its use and a method for controlling weeds.

18 Claims, No Drawings

CONCENTRATED STABLE SUSPENSION OF HERBICIDALLY ACTIVE 1,3,5-TRIAZINES AND PYRIDATE

The invention relates to a herbicidally active, concentrated, stable suspension of 1,3,5-triazines, pyridate, organic solvents and emulsifiers.

It is known that various 1,3,5-triazines have excellent herbicidal properties. Due to the application of these products often for decades, many harmful plants have become resistant, so that they can no longer be controlled even when applying high dosages of active substance. It is also known that the problem of resistance can be solved to a large extent through the combined application of e.g. atrazine with the compound 6-chloro-3-phenylpyridazin-4-yl-5-octyl-thiocarbonate ("pyridate").

This combined application previously took place in two ways. Firstly, in the form of tank mixtures, whereby the commercially obtainable formulations of both individual active substances are diluted with water to the application concentration directly before they are taken to the field. Such tank mixtures have the disadvantage for the manufacturer that two separate formulations must be produced and packaged, and for the user that two packages must be stored and handled. Furthermore, there is a danger of incorrect dosaging, if the farmer uses both products together, the products often being supplied by different manufacturers, since the individual active substances usually require a dosage other than that of their combination.

Secondly, in the form of a ready-mixed formulation, which is produced by absorbing pyridate, which is liquid at room temperature, onto an absorbing carrier material, e.g. highly dispersed silicic acid, mixing it with wetting and dispersing agents and with the solid atrazine, and grinding the mixture to a wettable powder. This product has the trade name "PRADO WP". It is true that dilution to the application concentration is simpler in this case, and there is less danger of incorrect dosaging, but it has turned out that both with the tank mixture and with the ready-mixed formulation as a wettable powder, some important weeds cannot be satisfactorily controlled with the recommended application rates.

It was therefore the aim of the present invention to find a stable formulation, which would satisfactorily control all important weeds, and with which improved action against weeds might be obtained whilst applying a smaller amount of the individual active substances.

It was unexpectedly found that a suspension of herbicidally active 1,3,5-triazines in a solution of pyridate complies with these requirements.

The invention thus relates to a concentrated stable suspension of herbicidally active 1,3,5-triazines in a solution of pyridate in an organic solvent or solvent mixture, in which pyridate at 0° C. is at least 10% by weight soluble and the 1,3,5-triazines are at most 1% by weight soluble, together with emulsifiers.

Pyridate is the compound 6-chloro-3-phenylpyridazin4-yl-5-octyl-thiocarbonate. Herbicidally active 1,3,5-triazines are for example atrazine, terbuthylazine, simazine, propazine and cyanazine.

On the one hand, pyridate should be as soluble as possible in the organic solvent, namely at 0° C. at least 10% by weight, preferably at least 20% by weight. There are no upper limits to the solubility of pyridate, but it is usually not more than 50% by weight. The solubility at 0° C. is more important than the solubility at 20° C., since the formulation must also have good cold stability. Pyridate must be chemically inert towards the organic solvent or solvent mixture. On the other hand, the 1,3,5-triazine should form as good a suspension as possible in the organic solvent and should be as insoluble as possible therein, so that there is no crystal growth with temperature variations. For this reason, the solubiity of the triazine at 0° C. should be less than 1% by weight, preferably less than 0.1 by weight.

Examples of such organic solvents or solvent mixtures are: n-paraffins having 6–14 C-atoms, paraffinic mineral oils with a boiling point range between 100° and >400° C., which consist of n- and/or i-paraffins and/or cycloaliphatics and may contain 0–50% aromatic substances, aromatic oils with 50–100% aromatic substances with a boiling point range between 130° and 280° C., especially aromatic oils, as well as oils of vegetable origin, e.g. rapeseed oil, sunflower oil, soybean oil, peanut oil, cottonseed oil, corn oil and others. Furthermore, alkyl esters, especially lower alkyl esters of fatty acids, e.g. rapeseed oil methyl ester or mixtures of vegetable oils and vegetable oil fatty acid alkyl esters, as well as mixtures of these solvents.

Suitable emulsifiers are those which on the one hand efficiently emulsify the solution of pyridate in the organic solvent when it is added to water, and on the other hand disperse the dispersed solid, the 1,3,5-triazine, in such a way that a stable, non-flocking suspo- emulsion is produced, from which neither oil nor solid separates.

Combinations which have proved to be particularly good are those of ionic and non-ionic emulsifiers, such as mixtures of straight-chain and branched Ca-dodecylbenzene sulphonate with ethoxylated alkylphenol, such as nonylphenol ethoxylates with 4–8 mols of ethylene oxide, or octylphenol ethoxylates with 4–8 mols of ethylene oxide, or mixtures of straight-chain or branched Ca-dodecylbenzene sulphonate with polyoxyethylene-sorbitan-fatty acid esters, or mixtures of straight-chain or branched Ca-dodecylbenzene sulphonate with ethoxylated castor oil with 5–80 mols of ethylene oxide. Furthermore, mixtures of straight-chain or branched Ca-dodecylbenzene sulphonate with ethoxylated and propoxylated linear or branched alcohol with 4–18 C-atoms and 2–50 mols of ethylene oxide resp. propylene oxide, as well as mixtures of the mixtures listed. =p Since oily suspensions are inclined to deposit the solid to a greater or lesser extent depending on the viscosity, it is advantageous to add thickening or anti-sedimentation assistants to the formulation. Suitable assistants of this kind are for example: pyrogenic silicic acid (Aerosil 200 from the company Degussa or Cabosil from the company Cabot), pyrogenic silicic acid which has been rendered hydrophobic (e.g. Aerosil R972, Aerosil R974), finely ground precipitated silicic acid (e.g. Wessalon S from the company Degussa), finely ground precipitated silicic acid which has been rendered hydrophobic (e.g. Wessalon D17 from the company Degussa), pyrogenic aluminium oxide (e.g. aluminium oxide C from the company Degussa), attapulgite clays such as Attagel 50 or Attasorb from the company Engelhardt, betonites, very finely ground talcum.

To produce the concentrated, stable suspension, pyridate and emulsifier or emulsifier mixture are dissolved in the organic solvent or solvent mixture whilst stirring, whereupon the 1,3,5-triazine and optionally the anti-sedimentation assistant are added to the homogeneous solution obtained and stirred until the solid is finely distributed. In order to reduce the particle size of the solid, the product is subsequently wet-ground in a pearl mill.

The pyridate content in the finished, concentrated, stable suspension is 1–80% by weight, preferably 10–30% by weight, and the triazine content therein is 1–60% by weight, preferably 10–30% by weight.

The formulations according to the invention are very stable in storage. The sediment resp. supernatant formed even after 12 weeks storage at 40° C. can be completely eliminated by gentle agitation, whereby the essential physical parameters, such as viscosity or emulsion stability, remain substantially unchanged.

A. PREPARATION EXAMPLES

Example 1

20 parts by weight of pyridate, 10 parts by weight of an emulsifier mixture consisting of 8 parts by weight of an ethoxylated nonylphenol with 6 mols of ethylene oxide and 2 parts by weight of a linear Ca-dodecylbenzene sulphonate are dissolved in 54 parts by weight of a paraffinic mineral oil having a boiling point range of 350° to 460° C. at normal pressure and a kinematic viscosity of 44 mm$^2$/sec at 20° C. Then, 16 parts by weight of atrazine are added and stirred, until a homogeneous suspension is produced. In order to reduce the particle size of the atrazine and thus reduce sedimentation, this suspension is subsequently wet-ground in a pearl mill, until reaching a viscosity of 1500 mPa.sec, measured on a Brookfield LVT viscosimeter with spindle 2 at 6 rpm. A 1% dispersion of this formulation in hard and soft water indicated good stability. After one hour, there was no separation of cream or oil and no sedimentation of solids.

Example 2

15 parts by weight of pyridate and 10 parts by weight of an emulsifier mixture consisting of 6 parts by weight of an ethoxylated nonylphenol with 6 mols of ethylene oxide, 3 parts by weight of an ethoxylated castor oil with 25 mols of ethylene oxide and 1 part by weight of a linear Ca-dodecylbenzene sulphonate are dissolved in 50 parts by weight of a mineral oil mixture consisting of 25% aromatic hydrocarbons with a boiling point range of 180° to 200° C. and 75% paraffinic and cycloaliphatic hydrocarbons with a boiling point range of 185° to 215° C. Afterwards, 25 parts by weight of atrazine are added and stirred, until a homogeneous suspension was produced. In order to reduce the particle size of the atrazine and thus reduce sedimentation, the suspension is subsequently wet-ground in a pearl mill, until reaching a viscosity of 1500 mPa. sec, measured on a Brookfield LVT viscosimeter with spindle 2 at 6 rpm. The formulation dispersed spontaneously upon pouring into water. A 1% dispersion of this formulation indicated the same stability as described under example 1.

Example 3

15 parts by weight of pyridate, 10 parts by weight of an emulsifier mixture consisting of 7 parts by weight of an ethoxylated nonylphenol with 6 mols of ethylene oxide, 2 parts by weight of an ethoxylated castor oil with 25 mols of ethylene oxide and 1 part by weight of a linear Ca-dodecylbenzene sulphonate are dissolved in 50 parts by weight of an oil consisting of a mixture of rapeseed oil and rapeseed oil methyl ester in a weight ratio of 1:1. Then, 25 parts by weight of atrazine are added and the mixture is stirred, until a homogeneous suspension is produced. In order to reduce the particle size of the atrazine and thus reduce sedimentation, the suspension is subsequently wet-ground in a pearl mill, until reaching a viscosity of 2000 mPa.sec, measured on a Brookfield LVT viscosimeter with spindle 2 at 6 rpm. The formulation dispersed spontaneously upon pouring into water. A 1% dispersion of this formulation indicated the same stability in hard and soft water as the formulation according to example 1.

Example 4

20 parts by weight of pyridate, 10 parts by weight of an emulsifier mixture consisting of 2 parts by weight of an ethoxylated oleic acid sorbitan ester with 20 mols of ethylene oxide, 1 part by weight of an ethoxylated castor oil with 25 mols of ethylene oxide and 7 parts by weight of a linear Ca-dodecylbenzene sulphonate are dissolved in 55 parts by weight of an oil consisting of a mixture of rapeseed oil and rapeseed oil methyl ester in a weight ratio of 1:1. Then, 15 parts by weight of atrazine are added and the mixture is stirred, until a homogeneous suspension was produced. The suspension is wet-ground. The formulation dispersed spontaneously upon pouring into water. A 1% dispersion of this formulation indicated the same stability as the formulation according to example 1.

Example 5

16 parts by weight of pyridate, 10 parts by weight of an emulsifier mixture consisting of 7 parts by weight of an ethoxylated nonylphenol with 6 mols of ethylene oxide, 2 parts by weight of an ethoxylated castor oil with 25 mols of ethylene oxide and 1 part by weight of a linear Ca-dodecylbenzene sulphonate are dissolved in 50 parts by weight of an oil consisting of a mixture of rapeseed oil and rapeseed oil methyl ester in a weight ratio of 1:1. Then, 25 parts by weight of terbuthylazine are added and the mixture is stirred, until a homogeneous suspension is produced. In order to reduce the particle size of the terbuthylazine and thus reduce sedimentation, the suspension is subsequently wet-ground in a pearl mill, until reaching a viscosity of 2000 mPa.sec, measured on a Brookfield LVT viscosimeter with spindle 2 at 6 rpm. The formulation dispersed spontaneously upon pouring into water. A 1% dispersion of this formulation indicated the same stability in hard and soft water as the formulation according to example 1.

Example 6

30 parts by weight of pyridate, 11 parts by weight of an emulsifier mixture consisting of 9 parts by weight of an ethoxylated nonylphenol with 6 mols of ethylene oxide and 2 parts by weight of a linear Ca-dodecylbenzene sulphonate are dissolved in 42.3 parts by weight of a paraffinic mineral oil with a boiling point range of 350° to 460° C. at normal pressure and a kinematic viscosity of 44 mm2/sec at 20° C. Then, 16.7 parts by weight of terbuthylazine are added and the mixture is stirred, until a homogeneous suspension was produced. This is wet-ground. A 1% dispersion of this formulation indicated the same stability as the formulation according to example 1.

Example 7

20 parts by weight of pyridate, 10 parts by weight of an emulsifier mixture consisting of 8 parts by weight of an ethoxylated nonylphenol with 6 mols of ethylene oxide and 2 parts by weight of a linear Ca-dodecylbenzene sulphonate are dissolved in 50 parts by weight of a paraffinic mineral oil with a boiling point range of 350° to 460° C. at normal pressure and a kinematic viscosity of 44 mm2/sec at 20° C. Then, 16 parts of atrazine and 4 parts of Attagel 50 as an anti-sedimentation additive are added and the mixture is stirred until a homogeneous suspension is produced. In order to reduce the particle size of the atrazine, the suspension is subsequently wet-ground in a pearl mill, until reaching a viscosity of 1500 mPa.sec, measured on a Brookfield LVT viscosimeter with spindle 2 at 6 rpm. This formulation was stored for 12 weeks at 40° C. in a sealed glass bottle, and afterwards the level of the sedimented atrazine resp. the level of the clear yellow supernatant was determined.

The supernatant was 9% of the total level and the suspension was homogenized again by gentle agitation. No sticky, non-redispersible sediment had formed.

Example 8

15 parts by weight of pyridate, 10 parts by weight of an emulsifier mixture consisting of 6 parts by weight of an ethoxylated nonylphenol with 6 mols of ethylene oxide, 3 parts by weight of an ethoxylated castor oil with 25 mols of ethylene oxide and 1 part by weight of a linear Ca-dodecylbenzene sulphonate are dissolved in 48 parts by weight of a mineral oil mixture consisting of 25% aromatic hydrocarbons with a boiling point range of 180° to 200° C. and 75% paraffinic and cycloaliphatic hydrocarbons with a boiling point range of 185° to 215° C. at normal pressure. Then, 25 parts by weight of atrazine and 2 parts of Aerosil R972 are added and the mixture is stirred, until a homogeneous suspension is produced. In order to reduce the particle size of the atrazine, this suspension is subsequently wet-ground in a pearl mill, until reaching a viscosity of 2500 mPa.sec, measured on a Brookfield LVT viscosimeter with spindle 2 at 6 rpm. This formulation was stored for 12 weeks at 40° C. in a sealed glass bottle, and afterwards the level of the sedimented atrazine resp. the level of the clear yellow supernatant was determined. The supernatant was 25% of the total level and the suspension was homogenized again by gentle agitation. No sticky, non-redispersible sediment had formed.

Example 9

10 parts by weight of pyridate, 11 parts by weight of an emulsifier mixture consisting of 9 parts by weight of an ethoxylated nonylphenol with 6 mols of ethylene oxide and 2 parts by weight of a linear Ca-dodecylbenzene sulphonate are dissolved in 49 parts by weight of a paraffinic mineral oil with a boiling point range of 350° to 460° C. at normal pressure and a kinematic viscosity of 44 mm$^2$/sec at 20° C. Then, 30 parts of simazine are added and the mixture is stirred until a homogeneous suspension was produced. In order to reduce the particle size of the simazine and thus to reduce sedimentation, the suspension as subsequently wet-ground in a pearl mill, until reaching a viscosity of 2000 mPa.sec, measured on a Brookfield LVT viscosimeter with spindle 2 at 6 rpm. A 1% dispersion of this formulation in hard and soft water indicated good stability. After one hour, there was no separation of cream or oil and no sedimentation of solids.

Comparison Example C1

Commercially obtainable wettable powder under the name LENTAGRAN WP. The formulation contains 45% pyridate.

Comparison Example C2

Commercially obtainable emulsion concentrate of pyridate under the name LENTAGRAN EC. The formulation contains 450 g/l pyridate.

Comparison Example C3

Commercially obtainable suspension concentrate of atrazine under the name LENTAZIN FLÜSSIG. The formulation contains 500 g/l atrazine.

Comparison Example C4

Commercially obtainable suspension concentrate of terbuthylazine under the name GARDOPRIM 500. The formulation contains 500 g/l terbuthylazine.

Comparison Example C5

Commercially obtainable wettable powder under the name PRADO WP. The formulation contains 25% pyridate and 20% atrazine.

Comparison Example C6

Wettable powder formulation of pyridate+terbuthylazine: 35 parts by weight of precipitated silicic acid and 13 parts by weight of kaolin were placed in a suitable mixer equipped with a device for spraying a liquid, and 25 parts by weight of liquid pyridate were sprayed thereon whilst mixing continuously. The pyridate was absorbed by the carrier material, and a freely flowing, dry powder was produced. Afterwards, 20 parts by weight of terbuthylazine, 5 parts by weight of Ca-lignin sulphonate, 2 parts by weight of Na-diisobutylnaphthalene sulphonate were mixed in, and the mixture formed was finely ground in a pin mill.

B. APPLICATION EXAMPLES

To compare the new formulations according to the invention with powder formulations and tank mixtures, tests were set out in the open under practical conditions. The test areas selected were maize fields with appropriate weed infestation. The guidelines of the Federal Office of Biology in Braunschweig were used as a basis for carrying out the field tests. The plot size was 19 m$^2$ (3.8×5.0 m). Application was effected with portable plot-spraying apparatuses driven by compressed air, with a spray bar of 4 m width and Teejet nozzle 11003. The amount of water applied was fixed at 300 l/ha at a spray pressure of 3.0 bar. Each variant was applied twice per site, whereby between the two repeated applications, an untreated control strip of 2 m width was omitted. Assessment of the tests was carried out by optical appraisals. The action of the individual variants against weeds was marked using the EWRC scale and subsequently expressed in % weed control using a known calculating method. In these field tests, the formulations according to the invention have stronger activity throughout, with the same or a reduced application rate of active substances, especially against harmful grasses such as the Echinocloa, Digitaria and Setaria types.

The results are summarised in examples 10–17.

In the tables, the following significances are applicable:

Active substances:

Pyr=pyridate

Ter=terbuthylazine

Atr=atrazine

Weeds:

AMARE=Amaranthus retroflexus

ANGAR=Anagallis arvensis

CHEAL=Chenopodium album

DIGIS=Digitaria ischaemum

ECHCG=Echinocloa crus-galli

FALCO=Fallopia convolvulus

GALAP=Galium aparine

GASPA=Galinsoga parviflora

LAPCO=Lapsana communis

MATCH=Matricari a chamomilla
POLAV=Polygonum aviculare
POLPE=Polygonum persicaria
SETVE=Setaria verticillata
SETVI=Setaria viridis
SOLNI=Solanum Nigrum

Example 10

Average from 5 Tests

| | application rate/ha | | | | | | |
|---|---|---|---|---|---|---|---|
| Ex. | product | active substance | active substance | AMARE | CHEAL | ECHCG | GASPA |
| C6 | 4.0 kg | 1000 g | Pyr | 100 | 100 | 70.7 | 100 |
| | | 800 g | Ter | | | | |
| 6 | 3.3 l | 990 g | Pyr | 100 | 100 | 80.0 | 100 |
| | | 551 g | Ter | | | | |

Example 11

Average from 5 Tests

| | application rate/ha | | | | | | |
|---|---|---|---|---|---|---|---|
| Ex. | product | active substance | active substance | AMARE | CHEAL | ECHCG | FALCO | GALAP |
| C5 | 3.0 kg | 750 g | Pyr | 99.3 | 99.0 | 8.9 | 100 | 100 |
| | | 600 g | Atra | | | | | |
| 1 | 3.75 l | 750 g | Pyr | 99.5 | 99.8 | 32.5 | 100 | 100 |
| | | 600 g | Atra | | | | | |

Example 12

Average from 5 Tests

| | application rate/ha | | | | | | |
|---|---|---|---|---|---|---|---|
| Ex. | product | active substance | active substance | CHEAL | ECHCG | GALAP | MATCH | POPLE |
| C2 | 1.5 l | 675 g | Pyr | 100 | 91.2 | 100 | 98.7 | 100 |
| C3 | 2.25 l | 1125 g | Atra | | | | | |
| 2 | 4.5 l | 675 g | Pyr | 100 | 92.5 | 100 | 100 | 100 |
| | | 1125 g | Atra | | | | | |
| 3 | 4.5 l | 675 g | Pyr | 100 | 100 | 100 | 100 | 100 |
| | | 1125 g | Atra | | | | | |

Example 13

Average from 2 Tests

| | application rate/ha | | | | | |
|---|---|---|---|---|---|---|
| Ex. | product | active substance | active substance | CHEAL | ECHCG | LAPCO |
| C2 | 1.5 l | 675 g | Pyr | 90 | 92.5 | 100 |
| C3 | 2.25 l | 1125 g | Atra | | | |
| 2 | 4.5 l | 675 g | Pyr | 95 | 98.7 | 100 |
| | | 1125 g | Atra | | | |
| 3 | 4.5 l | 675 g | Pyr | 90 | 97.5 | 100 |
| | | 1125 g | Atra | | | |

Example 14

Average from 2 Tests

| | application rate/ha | | | | | |
|---|---|---|---|---|---|---|
| Ex. | product | active substance | active substance | CHEAL | ECHCG | LAPCO |
| C2 | 1.5 l | 675 g | Pyr | 85 | 87.5 | 100 |
| C4 | 2.25 l | 1125 g | Ter | | | |
| 5 | 4.5 l | 675 g | Pyr | 85 | 96.2 | 100 |

Example 15

Average from 4 Tests

| Ex. | product | application rate/ha active substance | active substance | CHEAL | ECHCG | LAPCO |
|---|---|---|---|---|---|---|
| | | 1125 g | Ter | | | |

Example 16

Average from 5 Tests

| Ex. | product | application rate/ha active substance | active substance | AMARE | CHEAL | DIGIS | ECHCG | SETVE | SETVI |
|---|---|---|---|---|---|---|---|---|---|
| C1 | 3.0 kg | 1350 g | Pyr | 100 | 100 | 1.0 | 39.7 | 59.4 | 48.7 |
| C4 | 2.0 l | 1000 g | Ter | | | | | | |
| 5 | 4.0 l | 600 g | Pyr | 100 | 100 | 16.7 | 68.7 | 66.9 | 48.7 |
| | | 1000 g | Ter | | | | | | |

Example 17

Average from 3 Tests

| Ex. | product | application rate/ha active substance | active substance | CHEAL | AMARE | SOLNI | ANGAR | POLPE |
|---|---|---|---|---|---|---|---|---|
| C2 | 1.33 l | 600 g | Pyr | 97 | 98.3 | 99.3 | 100 | 36.7 |
| C3 | 1.5 l | 750 g | Atra | | | | | |
| 3 | 3.0 l | 450 g | Pyr | 99 | 99.1 | 99.3 | 100 | 60.0 |
| | | 750 g | Atra | | | | | |

| Ex. | product | application rate/ha active substance | active substance | POLAV | AMARE | MATCH | CHEAL |
|---|---|---|---|---|---|---|---|
| C2 | 1.0 l | 450 g | Pyr | 92.5 | 87.5 | 65 | 75 |
| C3 | 1.5 l | 750 g | Atra | | | | |
| 3 | 2.5 l | 375 g | Pyr | 90.0 | 82.5 | 70 | 75 |
| | | 625 g | Atra | | | | |
| 3 | 3.0 l | 450 g | Pyr | 96.5 | 90.0 | 70 | 85 |
| | | 750 g | Atra | | | | |

We claim:

1. Concentrated, stable suspension of herbicidally active 1,3,5-triazines in a solution of pyridate in organic solvents or mixtures thereof, in which at 0° C. pyridate is at least 10% by weight soluble and the 1,3,5-triazines are at most 1% by weight soluble, together with emulsifiers.

2. Concentrated, stable suspension according to claim 1, characterized in that at 0° C. pyridate is at least 20% by weight soluble in the organic solvents, and the 1,3,5-triazines are at most 0.1% by weight soluble therein.

3. Concentrated, stable suspension according to claim 1, characterized in that atrazine is used as the herbicidally active 1,3,5-triazine.

4. Concentrated, stable suspension according to claim 1, characterized in that terbuthylazine is used as the herbicidally active 1,3,5-triazine.

5. Concentrated, stable suspension according to claim 1, characterized in that the organic solvents are n-paraffins with 6–14 C-atoms, paraffinic mineral oils with a boiling point range between 100° and >400° C. with 0–50% aromatic substances, or aromatic oils with 50–100% aromatic substances, or mixtures thereof.

6. Concentrated, stable suspension according to claim 1, characterized in that the organic solvents are vegetable oils, alkyl esters of fatty acids, aromatic oils or mixtures thereof.

7. Concentrated, stable suspension according to claim 1, characterized in that the emulsifiers are a combination of ionic and non-ionic emulsifiers.

8. Concentrated, stable suspension according to claim 1, characterized in that it contains thickening or anti-sedimentation assistants.

9. Concentrated, stable suspension according to claim 1, characterized in that cyanazine is used as the herbicidally active 1,3,5-triazine.

10. Concentrated, stable suspension according to claim 1, characterized in that simazine is used as the herbicidally active 1,3,5-triazine.

11. Concentrated, stable suspension according to claim 1, characterized in that propazine is used as the herbicidally active 1,3,5-triazine.

12. A method of controlling harmful grasses in agriculturally used areas and set-aside areas comprising applying to said areas a concentrated suspension according to claim 1.

13. A method according to claim 12, wherein the harmful grasses to be controlled are Digitaria.

14. A method according to claim 12, wherein the harmful grasses to be controlled are Echinocloa.

15. A method according to claim 12, wherein the harmful grasses to be controlled are Setaria.

16. A method according to claim 12, wherein the herbicidally active 1,3,5-triazine is atrazine.

17. A method according to claim 12, wherein the agriculturally used area is a maize field.

18. A method according to claim 12, wherein the concentrated, stable suspension is diluted to the application concentration prior to application to the agriculturally used areas and set-aside areas.

* * * * *